United States Patent [19]

Trainor et al.

[11] Patent Number: 5,656,785
[45] Date of Patent: Aug. 12, 1997

[54] MICROMECHANICAL CONTACT LOAD FORCE SENSOR FOR SENSING MAGNITUDE AND DISTRIBUTION OF LOADS AND TOOL EMPLOYING MICROMECHANICAL CONTACT LOAD FORCE SENSOR

[75] Inventors: Christopher V. Trainor, Boxborough, Mass.; Steve T. Cho, Newport Beach, Calif.; Ralph E. Hopkins, III, Brookline, Mass.

[73] Assignee: The Charles Stark Draper Laboratory, Inc., Cambridge, Mass.

[21] Appl. No.: 511,658

[22] Filed: Aug. 7, 1995

[51] Int. Cl.⁶ .................................. G01D 7/00; G01L 3/00
[52] U.S. Cl. ............................. 73/862.046; 73/862
[58] Field of Search ........................... 73/760, 780, 862, 73/862.046, 862.473, 862.052

[56] References Cited

U.S. PATENT DOCUMENTS

| | | | |
|---|---|---|---|
| 4,503,705 | 3/1985 | Plochaninoff | 73/172 |
| 4,588,348 | 5/1986 | Beni et al. | 324/235 |
| 4,644,801 | 2/1987 | Kustanovich | 73/862.046 |
| 4,745,812 | 5/1988 | Amazeen et al. | 73/862.04 |
| 4,775,961 | 10/1988 | Capek et al. | 367/140 |
| 4,836,033 | 6/1989 | Seitz | 73/862.046 |
| 4,982,611 | 1/1991 | Lorenz et al. | 73/862.04 |
| 5,010,773 | 4/1991 | Lorenz et al. | 73/862.04 |
| 5,036,286 | 7/1991 | Holm-Kennedy et al. | 324/661 |
| 5,055,838 | 10/1991 | Wise et al. | 340/870.37 |
| 5,086,652 | 2/1992 | Kropp | 73/862.041 |
| 5,132,658 | 7/1992 | Dauenhauer et al. | 338/92 |
| 5,184,319 | 2/1993 | Kramer | 364/806 |
| 5,225,959 | 7/1993 | Stearns | 361/283 |
| 5,261,266 | 11/1993 | Lorenz et al. | 71/1 B |
| 5,503,029 | 4/1996 | Tamori | 73/862.046 |

OTHER PUBLICATIONS

K. Suzuki et al., "A 1024–Element High–Performance Silicon Tactile Imager", IEEE, 1988, pp. 674–677.

*Primary Examiner*—Richard Chilcot
*Assistant Examiner*—Max H. Noori
*Attorney, Agent, or Firm*—Weingarten, Schurgin, Gagnebin & Hayes LLP

[57] ABSTRACT

A micromechanical contact load force sensor is disclosed. The force sensor comprises an array of capacitive load cells on a substrate. The force sensor is able to sense high loads, on the order on $10^9$ $N/m^2$, and distribute the load over a suitable number of the cells of the array while minimizing crosstalk between adjacent cells. The force sensor is useful in biological and robotic applications.

36 Claims, 4 Drawing Sheets

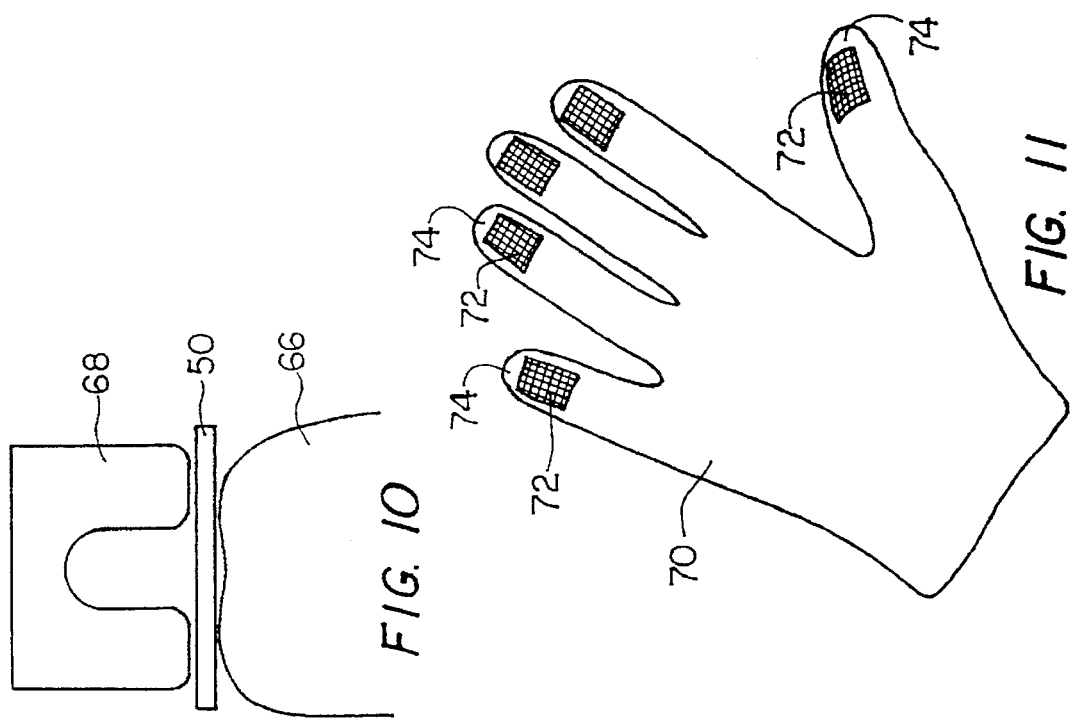
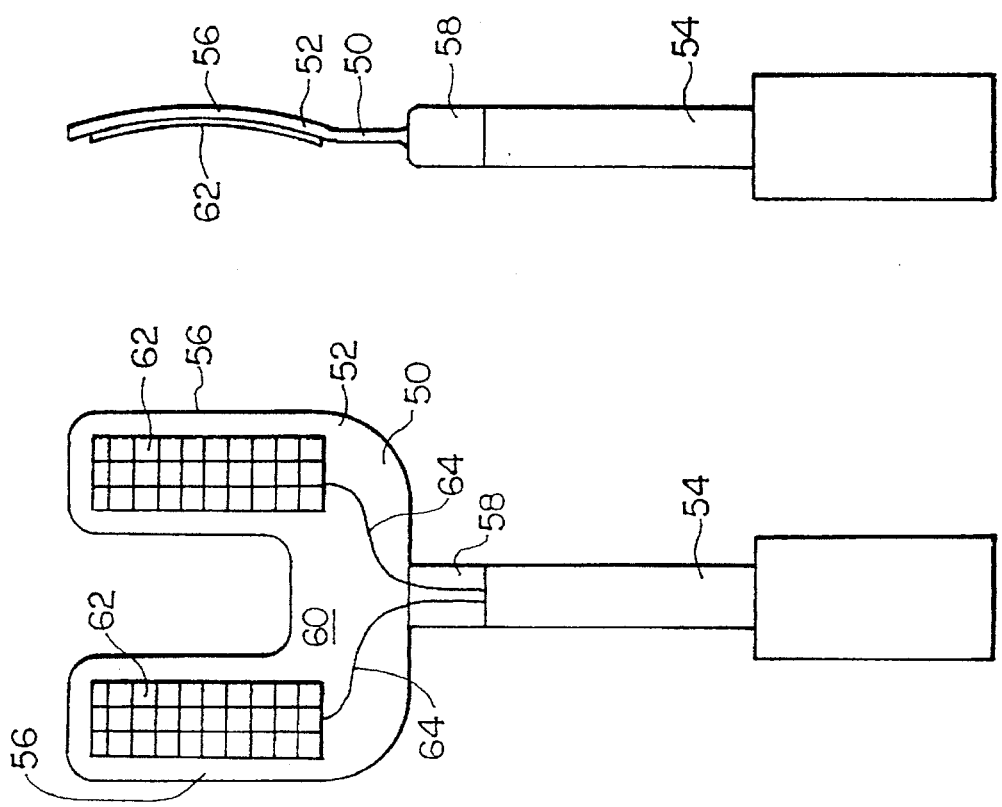

MICROMECHANICAL CONTACT LOAD FORCE SENSOR FOR SENSING MAGNITUDE AND DISTRIBUTION OF LOADS AND TOOL EMPLOYING MICROMECHANICAL CONTACT LOAD FORCE SENSOR

FIELD OF THE INVENTION

This invention relates to micromechanical devices and more particularly to micromechanical contact load force sensors.

BACKGROUND OF THE INVENTION

Load force sensors which use bulk sized load cells or sensitive films do not permit force measurement over very small areas, for example, on the order of a square centimeter, or enable a microscale array implementation which permits measurement of the force distribution over larger areas. Current micromechanical contact force sensors are suitable only for low load bearing applications. For example, U.S. Pat. No. 5,055,838 to Wise et al. discloses a micromechanical tactile imaging array comprising a bridge structure having a sensor plate which is 12.5 microns thick supported by thin flexible beams which are only 2.5 microns thick and deflect under a load on the sensor plate. U.S. Pat. No. 5,225,959 to Stearns discloses a capacitive tactile sensor array having a structure suitable for withstanding lower loads, on the order of $10^5$ N/m$^2$.

SUMMARY OF THE INVENTION

The present invention relates to a micromechanical device for measuring contact forces and force distribution between adjacent surfaces on the order of $10^9$ N/m$^2$. The device comprises an array of load cells formed from a large thickness of a semiconductor material, preferably silicon, thereby permitting both high sensitivity and high load bearing capacity. Each load cell incorporates a capacitor. The cells deflect under an applied load, and the deflection is measured by a change in the cell capacitive pickoff. The capacitance changes give a measure of the applied load through the mechanical stiffness of each array cell.

The force sensor includes an insulating substrate, preferably glass, and an array of capacitive load cells formed on the glass substrate. The load cells include a plurality of metal pads forming first capacitive plates laid down on the glass substrate in a spaced array. The plates are in electrical communication in columns. The silicon is bonded to the glass substrate and incorporates a boron-diffused layer to form a plurality of second capacitive plates overlying associated ones of the first capacitive plates with a capacitive gap therebetween. The silicon extends as a continuous mass above each of the first and second capacitive plates to form a deflective temple and incorporates a bearing surface or pad thereon for receiving the load. The silicon is electrically isolated in columns and has a plurality of valleys between adjacent temples to separate the adjacent bearing surfaces while allowing electrical communication in rows through the silicon. The silicon extends as a continuous mass from a low point of each of the valleys to the glass substrate.

The deflective temples and pads are formed of a sufficient thickness to withstand deflection of the silicon under a load on the order of $10^9$ N/m$^2$. The depth of the valleys along with the spacing between cells is chosen to distribute an applied load over a suitable number of cells while minimizing crosstalk between the cells, i.e., deflection of a cell due to a force on a neighboring cell.

A protective coating allows the device to measure forces on sensitive surfaces such as in biological applications. The microscale of the device permits contact force measurement in a minimally invasive fashion. The force sensor is particularly suitable for biological applications, such as a force balance sensing tool for use during total knee arthroplasty. The force sensor can also be used in robotic applications, such as robotic hands or gloves.

DESCRIPTION OF THE DRAWINGS

The invention will be more fully understood from the following detailed description taken in conjunction with the accompanying drawings in which:

FIG. 8 is a plan view of a force balance measuring tool employing the contact load force sensor of the present invention for total knee arthroscopy;

FIG. 9 is a side view of the tool of FIG. 8;

FIG. 10 is a schematic illustration of the tool of FIG. 8 employed during total knee arthroscopy; and FIG. 11 is a schematic illustration of a robotic glove employing the contact load force sensor of the present invention.

DETAILED DESCRIPTION OF THE INVENTION

Figure 1:
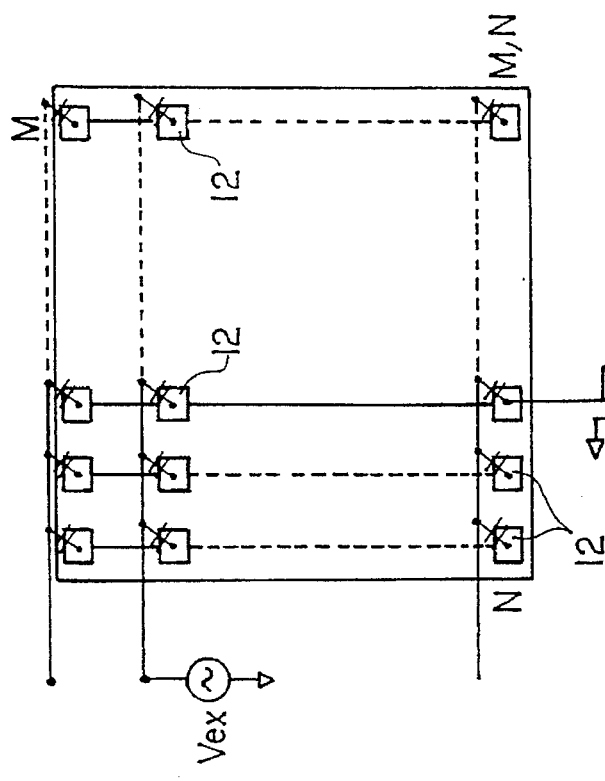
FIG. 1 is schematic plan view of a contact load force sensor of the present invention.
Figure 3:
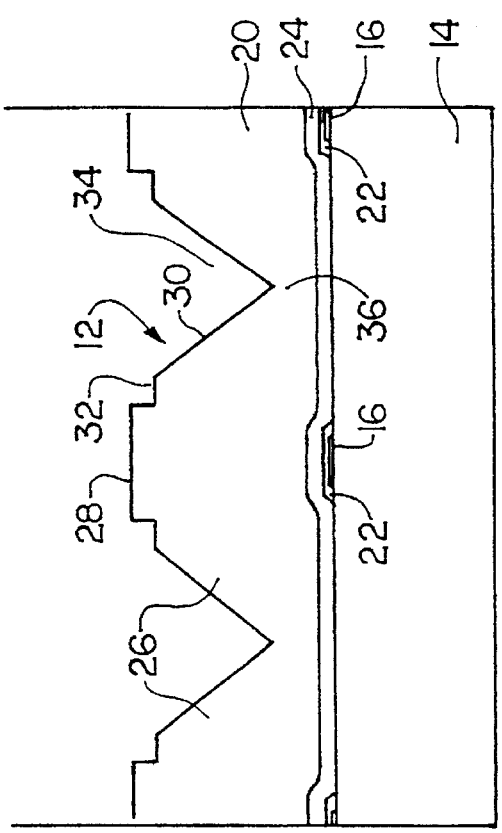
FIG. 3 is a schematic illustration of the circuitry of the contact load force sensor of FIG. 1.

FIG. 1 shows a force sensing or tactile array 10 having N rows and M columns of load cells 12, each incorporating a capacitor, microfabricated from a semiconductor material. The cells deflect under an applied load, and the deflection is measured by a change in the cell capacitive pickoff, as indicated in FIG. 3. The capacitance changes give a measure of the applied load through the mechanical stiffness of each array cell.

Figure 2:
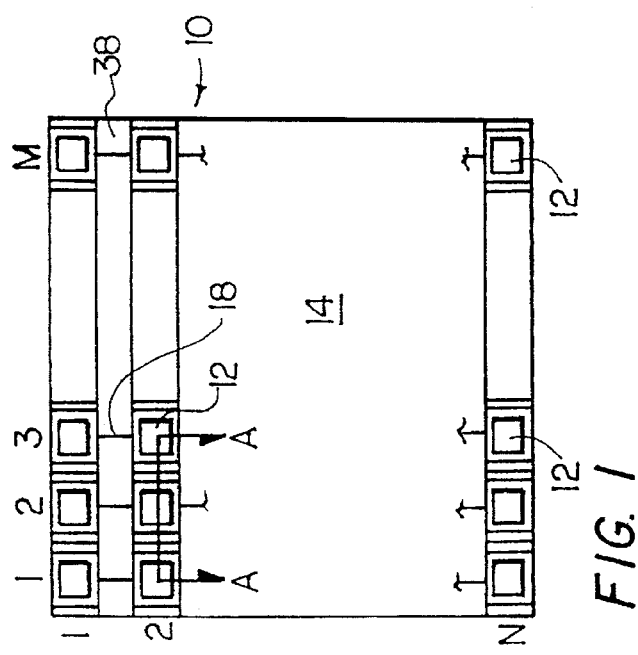
FIG. 2 is cross-sectional view along line A—A of FIG. 1.

More specifically, referring to FIGS. 1 and 2, the array of load cells is formed on an insulating substrate 14 such as glass. The substrate should be able to resist deflection under the loads for which the load cells are designed to deflect. Metal pads 16 connected in columns by strips 18 of metal for electrical communication are laid down on the glass substrate. Each metal pad forms one of the capacitive plates of each load cell.

A single crystal of a semiconductor material 20, preferably silicon, forms the deflective portion of each load cell. A plurality of recesses 22 is formed in an array configuration in the silicon to define the capacitive gaps for each load cell. A layer 24 of boron or other suitable material, such as phosphorous, antimony, arsenic, gallium, indium, or aluminum, diffused into the silicon forms the other of the capacitive plates for each cell. The boron-diffused side of the semiconductor material is bonded, as by anodic bonding, to the glass 14 with each metal pad 16 located within an associated recess or capacitive gap 22.

Figure 4:
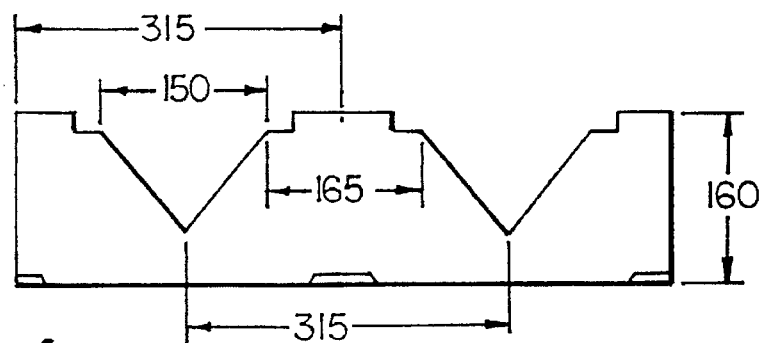
FIGS. 4 and 5 are cross-sectional views illustrating exemplary dimensions for the load force sensor of FIG. 1.
Figure 5:
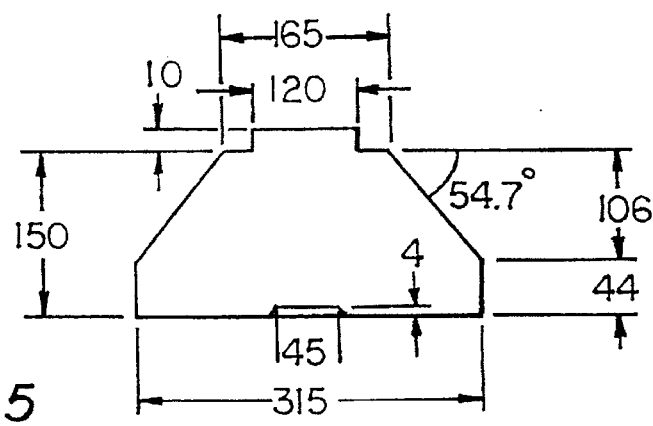

The silicon above the boron layer is configured to provide deflective structures, such as temples 26, formed as a continuous or substantially continuous mass extending above the capacitive plates. Each temple is surmounted by a bearing surface or pad. As shown in FIGS. 2, 4, and 5, the structures are in the form of temples having angled sides 30 and a shoulder 32 at the upper surface. However, other configurations, such as vertical sides are possible. The temples are separated from adjacent temples in the same row by valleys 34 extending parallel to the columns. The valleys do not extend completely through the silicon, thus providing a continuous or substantially continuous mass 36 of silicon below the valleys to the glass substrate, which increases the load bearing capacity of each cell. The continuous mass of silicon also provides an electrical connection along the rows. The deflective temples are electrically isolated in rows by trenches 38 parallel to the rows which extend completely through the silicon to the glass substrate.

Preferably, the pad or bearing surface 28 is centered above and overlies the edges of its associated capacitive gap 22. Under load, the temple 26 deflects sufficiently to reduce the width of the capacitive gap 22, which is detectable as a change in capacitance indicative of the magnitude of the load. The deflective temples 26 and pads 28 are formed of a sufficient thickness and sufficiently continuous mass of material to withstand deflection of the silicon under a load on the order of $10^9$ N/m$^2$. The depth and width of the valleys 34 along with the area and center-to-center spacing between pads 28 is chosen to distribute an applied load over a suitable number of cells while minimizing crosstalk between the cells, i.e., deflection of a cell due to a force on a neighboring cell.

A typical array may be 1 cm$^2$ and have 32 rows and 32 columns of load cells. To accommodate high loads on the order of $10^9$ N/m$^2$, the thickness of the silicon should be on the order of 100 µm. Preferably, the thickness is at least 100 µm. The dimensions in micrometers of a suitable load cell capable of bearing loads on the order of $10^9$ N/m$^2$ in an array without failure is shown in FIGS. 4 and 5. Such an array has a load capacity per cell, or force under which the maximum stress is reached, of 5.9 lb. The average stiffness of the cells is 3.04×10$^8$ N/m. The maximum deflection of each cell is 0.172 µm. The number of cells which can bear 20 lb. is 3.4 for a bearing element having a minimum radius of curvature of 189 mm. The crosstalk between cells is 0.02%, which is acceptable.

Figure 6:
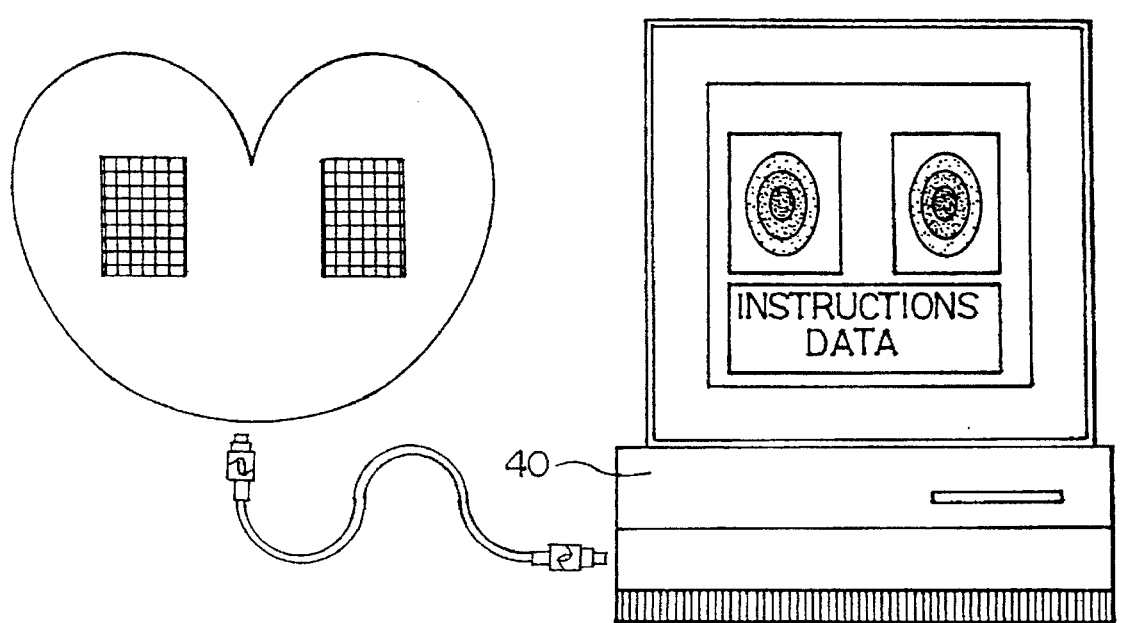
FIG. 6 is schematic illustration of a computer system and graphical display of sensed force data.

Referring to FIG. 3, during operation, the force data is acquired by sequentially addressing the array rows and columns to measure the pick-off capacitance of individual cells. The M,N cell is read out when the Mth column and Nth row are excited. Suitable circuitry, as is known in the art, is provided to read out and process the signals. The sensed information may be recorded on a computer 40 and graphically displayed to show contact force magnitude and location over the array, as indicated in FIG. 6. For example, various colors can be used to indicate forces of different magnitudes.

Figure 7:
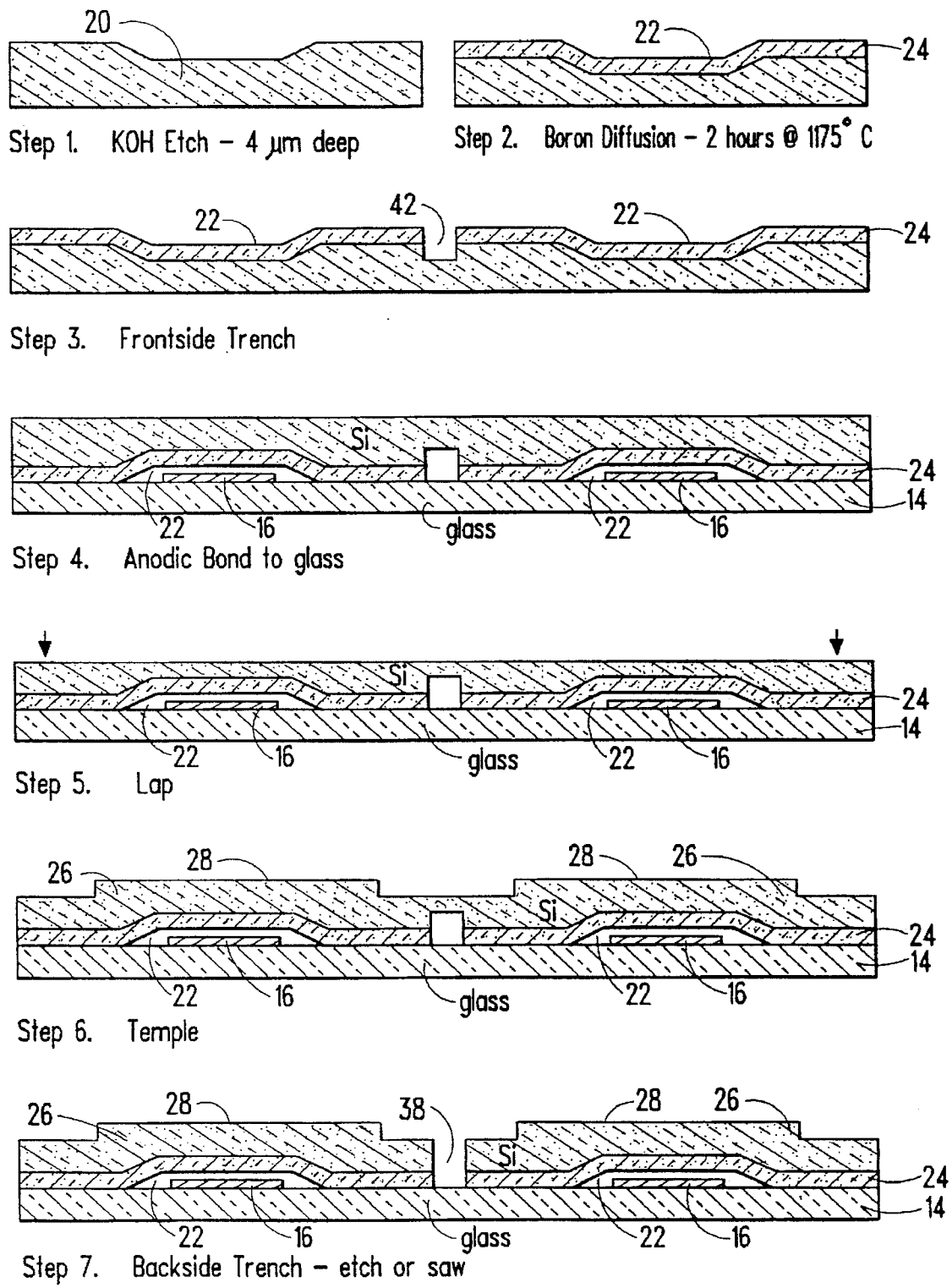
FIG. 7 is a schematic view illustrating exemplary fabrication steps for the load force sensor of FIG. 1.

An exemplary process for the fabrication of the tactile array of the present invention begins with the provision of a suitable semiconductor material 20 such as single crystal silicon, as shown in FIG. 7. The capacitive gaps 22 are formed in a surface of the silicon, as by a KOH etch. One of the capacitive plates is formed by a boron diffusion 24 for two hours at 1175° C. A frontside trench 42 is formed, as by etching or sawing, partially through the silicon to begin formation of the trenches 38 for electrical isolation of the silicon in rows.

A glass substrate 14 is metallized to provide the other of the capacitive plates 16 and the electrical connections between the plates in columns. The boron-diffused side of the silicon is anodically bonded to the glass with the capacitive gaps 22 overlying the metal capacitive pads 16. The silicon is lapped to the desired thickness for the deflective structures 26, for example, 160 microns. Further silicon is removed to form the desired configuration, such as the angled temple shape illustrated in FIGS. 2, 4, and 5. A backside trench is formed, as by etching or sawing, to connect with the frontside trench to form the trench 38 to electrically isolate the silicon in rows.

The load cells can be covered with a protective coating to enable the device to be used against sensitive surfaces such as are found in biological applications. Suitable coatings may be parylene or kynar.

The tactile array of the present invention is particularly suitable for measuring the contact forces at the interface of the tibial and femoral implants during total knee arthroplasty (TKA). TKA surgery requires the operating surgeon to adjust and trim soft tissue to balance the medial to lateral contact forces in the prosthetic knee implant. Typically, the surgeon relies on judgment and experience to align the implants and adjust soft tissue for knee force balance. No quantitative measurements of knee contact forces are available during surgery.

In the present invention, a tool 50 having a paddle 52 and a detachable handle 54 is provided as shown in FIGS. 8 and 9. The paddle has a U-shaped portion having two extending arms 56 and a base 58 to which the detachable handle may be attached. The U-shaped portion forms a substrate 60 on which two tactile arrays 62 as described above may be mounted. Any suitable material capable of bearing the forces of the intended application, such as a polyethylene, may be used to form the U-shaped portion. The U-shaped portion is curved in side view, as seen in FIG. 9, to conform to the shape of the prosthesis. Wires 64 extend from each tactile array to an electrical connection in the base 58 of the paddle.

The base 58 of the paddle 52 includes a detachable mechanical connection with the handle 54 and an electrical connection to a readout device. In this manner, the handle may be detached and the readout device connected to the electrical connection in the base to read out the location and magnitude of the forces between the parts.

In operation, illustrated in FIG. 10, the tool 50 is inserted between the tibial implant bearing surface and the femoral implant so that the pair of tactile arrays 62 are loaded by each side (medial and lateral) of the femoral prothesis. During surgery, the tactile arrays furnish quantitative measurements of the magnitude and location of the contact forces between the femoral 66 and tibial 68 implants, from which the medial to lateral force balance can be readily determined.

The tactile array of the present invention is also suitable for use in robotic applications such as on a robotic hand or on a robotic glove 70, as shown in FIG. 11. For example, an array 72 may be placed at each fingertip area 74 to sense forces when the glove is used to grasp an object.

The invention is not to be limited by what has been particularly shown and described, except as indicated by the appended claims.

We claim:

1. A micromechanical contact load force sensor comprising:
    an array of deformable capacitive elements connected in electrical communication in columns along an insulating substrate and in electrical communication in rows through a semiconductor material bonded to said substrate, said semiconductor material provided as an array of unitary bodies each extending continuously from said insulating substrate adjacent capacitive gaps to an array of isolated bearing surfaces above said capacitive gaps, each bearing surface positioned above an associated capacitive element of said array of capacitive elements to define an array of load cells, wherein a change in capacitance is effected by deformation of one of said unitary bodies above said capacitive gaps.

2. The micromechanical contact load force sensor of claim 1, wherein said bearing surfaces are isolated by valleys formed in said semiconductor material.

3. The micromechanical contact load force sensor of claim 2, wherein said bearing surfaces are spaced a predetermined distance and said valleys have a predetermined depth to minimize crosstalk between adjacent load cells.

4. The micromechanical contact load force sensor of claim 1, wherein said unitary bodies of semiconductor material have a thickness extending above said array of capacitive elements sufficient to support a load of approximately $10^9$ N/m$^2$.

5. The micromechanical contact load force sensor of claim 1, wherein said unitary bodies of semiconductor material have a thickness of at least 100 μm.

6. The micromechanical contact load force sensor of claim 1, wherein said insulating substrate is glass.

7. The micromechanical contact load force sensor of claim 1, wherein said semiconductor material is silicon.

8. The micromechanical contact load force sensor of claim 1, wherein each capacitive element of said array of capacitive elements comprises a first capacitive plate affixed to said substrate and a second capacitive plate spaced by a capacitive gap from said first capacitive plate and formed of an element diffused into said semiconductor material.

9. The micromechanical contact load force sensor of claim 8, wherein said element diffused into said semiconductor material comprises boron, phosphorous, antimony, arsenic, gallium, indium, or aluminum.

10. The micromechanical contact load force sensor of claim 8, wherein said first capacitive plate comprises a metal bonded to said substrate.

11. A micromechanical contact load force sensor comprising:

an insulating substrate;

an array of capacitive load cells formed on said insulating substrate, comprising:
  a plurality of first capacitive plates formed on said insulating substrate in a spaced array, said first capacitive plates further being in electrical communication in columns,
  a semiconductor material bonded to said insulating substrate, a plurality of second capacitive plates supported by said semiconductor material to overlie associated ones of said first capacitive plates with a capacitive gap therebetween, said semiconductor material extending as a deformable continuous mass from said insulating substrate on opposed sides immediately adjacent said capacitive gaps to a bearing surface above each of said first and second capacitive plates, said semiconductor material electrically isolated in columns, said semiconductor material having a plurality of valleys provided therein between adjacent bearing surfaces to separate said adjacent bearing surfaces while allowing electrical communication in rows through said semiconductor material, said semiconductor material extending as a continuous mass from a low point of each of said plurality of valleys to said insulating substrate.

12. The micromechanical load force sensor of claim 11, wherein said valleys are defined by angled side walls.

13. The micromechanical load force sensor of claim 11, wherein said continuous mass of semiconductor material extending above said first and second capacitive plates has a thickness sufficient to support a load of approximately $10^9$ N/m$^2$.

14. The micromechanical load force sensor of claim 11, wherein said continuous mass of semiconductor material extending above said first and second capacitive plates has a thickness of at least 100 μm.

15. The micromechanical load force sensor of claim 11, wherein said bearing surfaces are spaced a predetermined distance and said valleys have a predetermined depth to minimize crosstalk between adjacent load cells.

16. The micromechanical load force sensor of claim 11, wherein said insulating substrate is glass.

17. The micromechanical load force sensor of claim 11, wherein said semiconductor material is silicon.

18. The micromechanical load force sensor of claim 11, wherein said first capacitive plates are formed by a metal.

19. The micromechanical load force sensor of claim 11, wherein said second capacitive plates are formed by a boron-diffused layer in said semiconductor material.

20. A tool for sensing magnitude and distribution of loads comprising:

a support surface;

a tactile array of capacitive load cells comprising:
  an insulating substrate supported by said support surface;
  a plurality of first capacitive plates formed on said insulating substrate in a spaced array, said first capacitive plates further being in electrical communication in columns,
  a semiconductor material bonded to said insulating substrate, a plurality of second capacitive plates supported by said semiconductor material to overlie associated ones of said first capacitive plates with a capacitive gap therebetween, said semiconductor material extending as a deformable continuous mass from said insulating substrate on opposed sides immediately adjacent said capacitive gaps to a bearing surface above each of said first and second capacitive plates, said semiconductor material electrically isolated in columns, said semiconductor material having a plurality of valleys provided therein between adjacent bearing surfaces to separate said adjacent bearing surfaces while allowing electrical communication in rows through said semiconductor material, said semiconductor material extending as a continuous mass from a low point of each of said plurality of valleys to said insulating substrate.

21. The tool of claim 20, wherein said support surface comprises two arms, said tactile array being disposed on one of said arms, a further tactile array being disposed on another of said arms.

22. The tool of claim 21, wherein said arms are curved.

23. The tool of claim 20, further including a handle.

24. The tool of claim 23, wherein said handle is detachable.

25. The tool of claim 20, further comprising an electrical connection connectable to a readout device.

26. The tool of claim 20, wherein said tool is configured to comprise a total knee arthroplasty force balance sensing device.

27. The tool of claim 20, wherein said tool is configured to comprise a robotic hand.

28. The tool of claim 20, wherein said tool is configured to comprise a robotic glove.

29. The tool of claim 20, wherein said valleys are defined by angled side walls.

30. The tool of claim 20, wherein said continuous mass of semiconductor material extending above said first and second capacitive plates has a thickness sufficient to support a load of approximately $10^9$ N/m².

31. The tool of claim 20, wherein said continuous mass of semiconductor material extending above said first and second capacitive plates has a thickness of at least 100 microns.

32. The tool of claim 20, wherein said bearing surfaces are spaced a predetermined distance and said valleys have a predetermined depth to minimize crosstalk between adjacent load cells.

33. The tool of claim 20, wherein said insulating substrate is glass.

34. The tool of claim 20, wherein said semiconductor material is silicon.

35. The tool of claim 20, wherein said first capacitive plates are formed by a metal.

36. The tool of claim 20, wherein said second capacitive plates are formed by a boron-diffused layer in said semiconductor material.

* * * * *